Feb. 1, 1949. J. A. WICKERSHAM Plant Pat. 821
PEACH TREE
Filed July 1, 1947
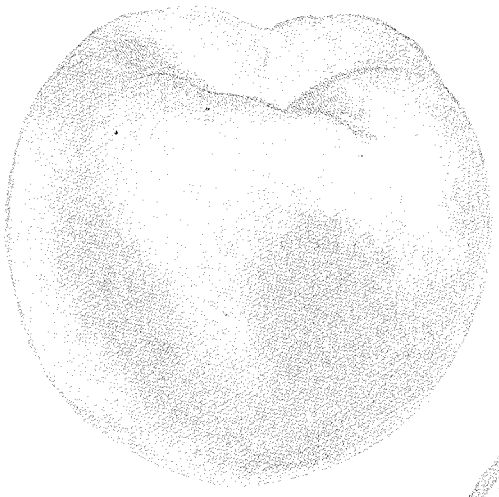
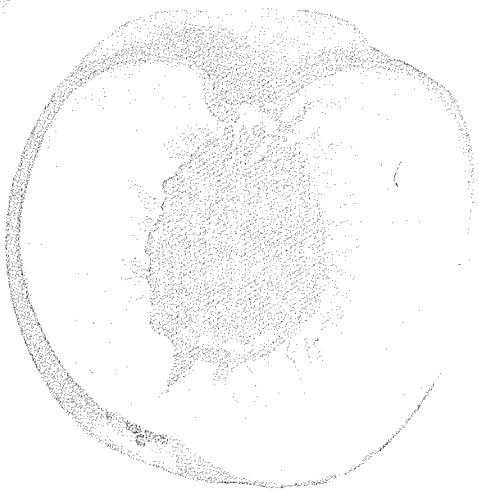
INVENTOR
Jesse A. Wickersham
By Orville M. Kile
PLANT PATENT AGENT Patented Feb. 1, 1949

Plant Pat. 821

UNITED STATES PATENT OFFICE

821

PEACH TREE

Jesse A. Wickersham, Yakima County, Wash.

Application July 1, 1947, Serial No. 758,331

1 Claim. (Cl. 47—62)

My present invention pertains to an improved variety of peach tree of the Elberta type, with particular reference to improvement in flavor, sugar content, coloring and keeping qualities of its fruit.

The flavor of its fruit is distinctive and difficult to describe verbally or to compare with the flavor of any other peach, but some of its qualities are that it is subacid, mild and delicate.

Because of the very high sugar content of the fruit it is an unusually delicious peach for eating raw; also much less sweetening is required when used for canning.

The fruit is attractive, being of the J. H. Hale type in shape and size. It most resembles the Elberta in color, but has a little more red. It excels in keeping qualities as is evidenced by the fact that I kept some for 30 days in perfect condition for eating in the natural raw state without the use of cold storage or any artificial preservative.

The parentage of my new variety is unknown. It originated as a chance seedling in a vicinity where only Elberta trees were growing, although is was found at the discharge end of an irrigation pipe where the seed might have been washed down from some other source.

The variety has been asexually reproduced by budding and the characteristic qualities have proved to be firmly fixed.

The drawing shows an elevation and a vertical section of a specimen of fruit of this variety.

Following is a detailed description of the tree, flowers and fruit of my new variety. Where colors are mentioned, ordinary dictionary meaning of the term is intended.

*The tree*

Growth: Vigorous, dense and spreading, with rounded top. Similar to Elberta.

Trunk: Stocky and smooth.

Branches: Stocky. Lenticels small to medium. Old wood brown and new wood glossy green.

Foliage:

*Size.*—Large, measuring 6 to 7 inches long and 1 to 1½ inches wide.

*Shape.*—Obovate and acutely pointed.

*Texture.*—Medium and smooth.

*Color.*—Dark green.

*Margin.*—Finely serrated.

*Petiole.*—Medium in length and size.

*Glands.*—Two reniform glands on opposite sides at base of leaf. Medium in size and green in color.

*Stipules.*—Medium in size; reddish-green.

Hardiness: Very hardy in this climate.

Productivity: Medium crop, but regular bearer each year.

Disease resistance: Good.

Insect resistance: Good.

*Flowers*

Buds:

*Size.*—Medium.

*Shape.*—Plump.

*Aspect.*—Pubescent.

Blossoms:

*Size.*—Medium.

*Color.*—Salmon-pink; Elberta and Hale type.

*Blooming dates.*—Late. First in full bloom here April 1st to 6th.

*Fruit*

Maturity dates and dates described: Picked September 9th; eating ripe, September 12th.

Size: Large. Typical specimen measures 2⅞ inches axial diameter, 3 inches transverse diameter in both the suture plane and at right angles to the suture plane.

Form: Uniformly globose or blocky, with rounded truncate base and short apical apex. Somewhat like the J. H. Hale in shape. Suture a shallow inconspicuous line showing on one side of cavity. Cavity rounded, about 1 inch across and ⅝ inch deep.

Stem: Length ⅜ to ½ inch; glabrous and adheres to stone moderately well.

Skin: Tough, free and of medium thickness. Fuzz scant. Color yellow with splashes of carmine; similar to Elberta in coloring but with more red.

Flesh:

*Color.*—Rich yellow, streaked with red next to stone. Surface of stone cavity is red with pink fibres.

*Texture.*—Firm, crisp, melting, and with few fibres.

*Flavor.*—Mild, delicate, subacid, distinctive. Sugar content is high compared to most peach varieties. Experts who have tasted this peach rate the flavor as superior to that of other varieties grown in this vicinity, both for canning and for eating raw.

Stone:

*Adherence.*—Free, but retains short fibres along ridges.

*Size.*—Large, approximately 1¾ inches long, 1¼ inches wide, and ¾ inch thick.

*Form.*—Oval with cuneate apex and oblique base. Sides equal; ventral edge winged toward base, dorsal edge narrow and grooved to above center.

*Surface.*—Irregularly furrowed throughout.

*Color.*—Red where in contact with flesh; brown where free.

*Tendency to split.*—Only slight.

Keeping quality: Excellent keeper. Tests have shown the fruit to be in perfect condition for raw eating after having been kept for 30 days without resorting to cold storage.

Shipping quality: Good, resulting principally from the good keeping quality and the tough skin.

Having thus disclosed my invention, I claim:

The new and distinct variety of peach tree of the Elberta type as herein disclosed, characterized particularly by its blocky, highly colored fruit having a distinctive mild flavor, very high sugar content, and unusually good keeping qualities.

JESSE A. WICKERSHAM.

No references cited.